United States Patent
Stier

(10) Patent No.: US 6,723,304 B2
(45) Date of Patent: Apr. 20, 2004

(54) ORAL CARE COMPOSITIONS COMPRISING DIGLYCEROL

(75) Inventor: Roger E. Stier, Clifton, NJ (US)

(73) Assignee: Noville, Inc., Hackensack, NJ (US)

( * ) Notice: Subject to any disclaimer, the term of this patent is extended or adjusted under 35 U.S.C. 154(b) by 0 days.

(21) Appl. No.: 10/266,493

(22) Filed: Oct. 8, 2002

(65) Prior Publication Data

US 2003/0095931 A1 May 22, 2003

Related U.S. Application Data

(63) Continuation-in-part of application No. 10/008,844, filed on Nov. 13, 2001, now abandoned.

(51) Int. Cl.[7] .......................... A61K 7/16; A61K 31/08
(52) U.S. Cl. ........................ 424/49; 424/48; 424/50; 424/51; 424/52; 424/53; 424/54; 424/55; 424/56; 424/57; 424/58; 514/723
(58) Field of Search ............................ 424/48, 49–58, 424/723; 514/723

(56) References Cited

U.S. PATENT DOCUMENTS

| | | |
|---|---|---|
| 2,584,307 A | 2/1952 | Tice |
| 2,975,102 A | 3/1961 | Matsumura et al. |
| 3,523,130 A | 8/1970 | Jones et al. |
| 3,840,656 A | 10/1974 | Kalopissis et al. |
| 3,873,686 A | 3/1975 | Beekman |
| 3,876,758 A | 4/1975 | Beekman |
| 4,556,557 A | 12/1985 | Reichert |
| 4,726,943 A | 2/1988 | Klueppel et al. |
| 4,829,092 A | 5/1989 | Nelson et al. |
| 4,960,953 A | 10/1990 | Jakobson et al. |
| 4,973,763 A | 11/1990 | Jakobson et al. |
| 5,041,688 A | 8/1991 | Jakobson et al. |
| 5,342,617 A | 8/1994 | Gold |
| 5,368,847 A | 11/1994 | Brunetta et al. |
| 5,449,551 A | 9/1995 | Taniguchi |
| 5,456,863 A | 10/1995 | Bergmann |
| 5,474,776 A | 12/1995 | Koyanagi et al. |
| 5,538,720 A | 7/1996 | Jendryssek-Pfaff et al. |
| 5,650,166 A | 7/1997 | Ribier et al. |
| 5,709,849 A | 1/1998 | Ito et al. |
| 5,750,120 A | 5/1998 | Miguel-Colombel |
| 5,874,092 A | 2/1999 | Roulier et al. |
| 5,902,590 A | 5/1999 | Thomas et al. |
| 5,935,384 A | 8/1999 | Taniguchi |
| 5,989,573 A | 11/1999 | Remy |
| 6,001,341 A | 12/1999 | Genova et al. |
| 6,036,968 A | 3/2000 | Roulier et al. |
| 6,042,844 A | 3/2000 | Ishida et al. |
| 6,045,781 A | 4/2000 | Bungard et al. |
| 6,117,434 A | 9/2000 | Oyama et al. |
| 6,126,928 A | 10/2000 | Swaile |
| 6,146,647 A | 11/2000 | Aoyama et al. |
| 6,180,124 B1 | 1/2001 | Ohta et al. |
| 6,206,902 B1 | 3/2001 | Morikane |
| 6,221,382 B1 | 4/2001 | Ishida et al. |
| 6,419,962 B1 | 7/2002 | Yokoyama et al. |
| 6,569,439 B1 | 5/2003 | Stier |
| 6,579,543 B1 | 6/2003 | McClung |
| 2003/0044359 A1 | 3/2003 | Wuelknitz et al. |

OTHER PUBLICATIONS

Product Data Sheet—Diglycerol—Solvay Interox web page (2001).
Abstract of Kapsalis et al., NATO ASI Ser. E. 90: 481–496 CAPLUS:576212 (1985) CA. 103:176212 1985.
Abstract of Babayan, Food Prod. Develop. 2(2); 58, 60–61–64 CAPLUS 418091 (1968) CA.69:18091 1968.

*Primary Examiner*—Frederick Krass
(74) *Attorney, Agent, or Firm*—Norris, McLaughlin & Marcus

(57) ABSTRACT

The invention relates to oral care compositions such as toothpaste, gels, tooth powders, mouthwashes, mouth rinses, gums, mouth sprays and lozenges comprising diglycerol. The diglycerol is used as a humectant in the compositions. The compositions may further comprise water, flavoring agents, active compounds, emulsifier, alcohol, sweeteners, thickening agents, surfactants, suspending agents, astringent and toning drug extracts, flavor correctants, abrasives or polishes, deodorizing agents, preservatives, flavoring buffers, whitening agents, wound-healing and inflammation inhibiting substances, colorants, dyes, pigments, abrasives, polishes, antimicrobial agents, pH buffers and other additives and fillers.

30 Claims, 3 Drawing Sheets

ORAL CARE COMPOSITIONS COMPRISING DIGLYCEROL

CROSS REFERENCE TO RELATED APPLICATION

This application is a continuation-in-part of U.S. patent application Ser. No. 10/008,844, filed Nov. 13, 2001, now abandoned.

BACKGROUND OF THE INVENTION

1. Field of the Invention

The invention relates to oral care compositions comprising diglycerols which unexpectedly have an enhanced and/or prolonged smooth lasting effect such as long lasting flavor and cooling characteristics in the mouth. The diglycerol provides humectant and emollient properties to the compositions.

2. The Prior Art

Oral malodor, plaque, gingivitis, periodontal disease, and discoloration of the teeth, are all undesirable conditions that affect many people. Malodor of the oral cavity is also known as halitosis or bad breath and it is generally believed that the cause of this condition is due to the presence of anaerobic bacteria, especially gram-negative anaerobic bacteria, in the mouth. These bacteria will generate volatile sulfur compounds (VSC), which are known to cause breath malodor.

Three chemical compounds cause some breath malodor, specifically, hydrogen sulfide (H—S—H), methyl mercaptan ($CH_3$—S—H) and dimethyl sulfide ($CH_3$—S—$CH_3$). These compounds result from the degradation of epithelial cells and bacteria in the oral cavity. The polypeptide chains of the epithelial cell walls are composed of a series of amino acids including cysteine and methionine, which contain sulfur side chains. The death of microorganisms or epithelial cells results in degradation of the polypeptide chains into their amino acid components, especially cysteine and methionine. Cysteine and methionine are precursors to the formation of VSC.

Oral malodor not only comes from the posterior dorsal surface of the tongue but also from periodontal pockets. A person with gingivitis or periodontal disease may have increased oral malodor from disintegrated epithelial cells. Epithelial cells turn over faster if inflammation is present. Therefore, a larger number of these dead epithelial cells remain in the oral cavity and will degrade into the malodorous compounds. In addition VSC will also alter the epithelial barrier, permitting penetration of the barrier by antigenic substances.

Oral care compositions, such as toothpaste, gels, mouthwashes, mouth rinses, gums, mouth sprays and lozenges, are directed, completely or in part, towards alleviating the conditions in the mouth which cause malodor, generally by physical means, such as brushing teeth with a dentifrice or by chemical means. The effectiveness of oral care compositions is generally perceived as a function of both 1) the ability of the active components of the oral care composition in attacking the conditions which bring about oral malodor, plaque, gingivitis, periodontal disease, and discoloration of the teeth and 2) prolonged smooth lasting effect and long lasting flavor and cooling characteristics in the mouth perceived by the user. Dentifrice manufacturers are constantly seeking ways to prolong the smooth lasting effect and flavor and cooling characteristics of oral care compositions.

Humectants and emollients absorb and promote the retention of moisture from the air. Traditional humectants in oral care compositions are glycerol, sorbitol or glycols. One of the more common humectants used in oral care compositions is glycerol. Glycerol will absorb moisture in the mouth, which serves to diminish the overall smooth lasting effect perceived by the user.

Flavor and cooling effects result primarily from the incorporation of flavoring and cooling agents in the oral care compositions. The objective in increasing the flavoring and cooling effect of an oral care composition is to increase the time that the flavoring and/or cooling agents remain effective after the oral care composition is applied by the consumer. Expensive and cost prohibitive methods of encapsulation are generally the only known means of achieving this objective. A formulation which efficiently enhances the flavoring and cooling effects of oral care compositions without costly means such as encapsulation has long eluded the dentifrice and oral care industry.

Diglycerol has, to the inventor's knowledge, not been used in oral care compositions as a humectant or emollient, or otherwise. For example, U.S. Pat. No. 4,726,943 describes anti-caries compositions comprising phosphoric acid esters of alkoylated polyols, including diglycerol, as an active component with low molecular weight polyethylene glycols, glycerol and sorbitol as humectants in the composition.

An object of the invention was to develop oral care compositions, such as toothpaste, gels, mouthwashes, mouth rinses, gums, mouth sprays and lozenges, which have an enhanced and/or prolonged smooth lasting effect.

A further object of the invention was to develop oral care compositions that have long lasting flavor and cooling characteristics in the mouth.

Yet another object of the invention was to develop oral care compositions having enhanced prolonged smooth lasting effect and long lasting flavor and cooling characteristics in the mouth without the need for special processing or techniques, such as encapsulation.

These and other objects of the invention are achieved by the incorporation of diglycerol as a humectant and/or emollient in oral care compositions. The diglycerol may be used with other humectants and emollients in the compositions and can replace some or all of the traditional and conventional humectant components of oral care compositions. The oral care compositions comprising diglycerol have enhanced prolonged smooth lasting effect and/or long lasting flavor and cooling effect due in part to the characteristics of the diglycerol molecule and its interaction with flavoring agents, which may incorporate cooling agents, after application of the composition.

In the present Specification, all parts and percentages are on a weight/weight basis unless otherwise specified.

SUMMARY OF THE INVENTION

The invention pertains to oral care compositions comprising diglycerol which unexpectedly have an enhanced and/or prolonged smooth lasting effect such as long lasting flavor and cooling characteristics in the mouth. The diglycerol is a humectant and/or emollient in the composition and can be used with other humectants and emollients. The compositions can further comprise other ingredients, additives and fillers.

DETAILED DESCRIPTION OF THE INVENTION

Figure 1:
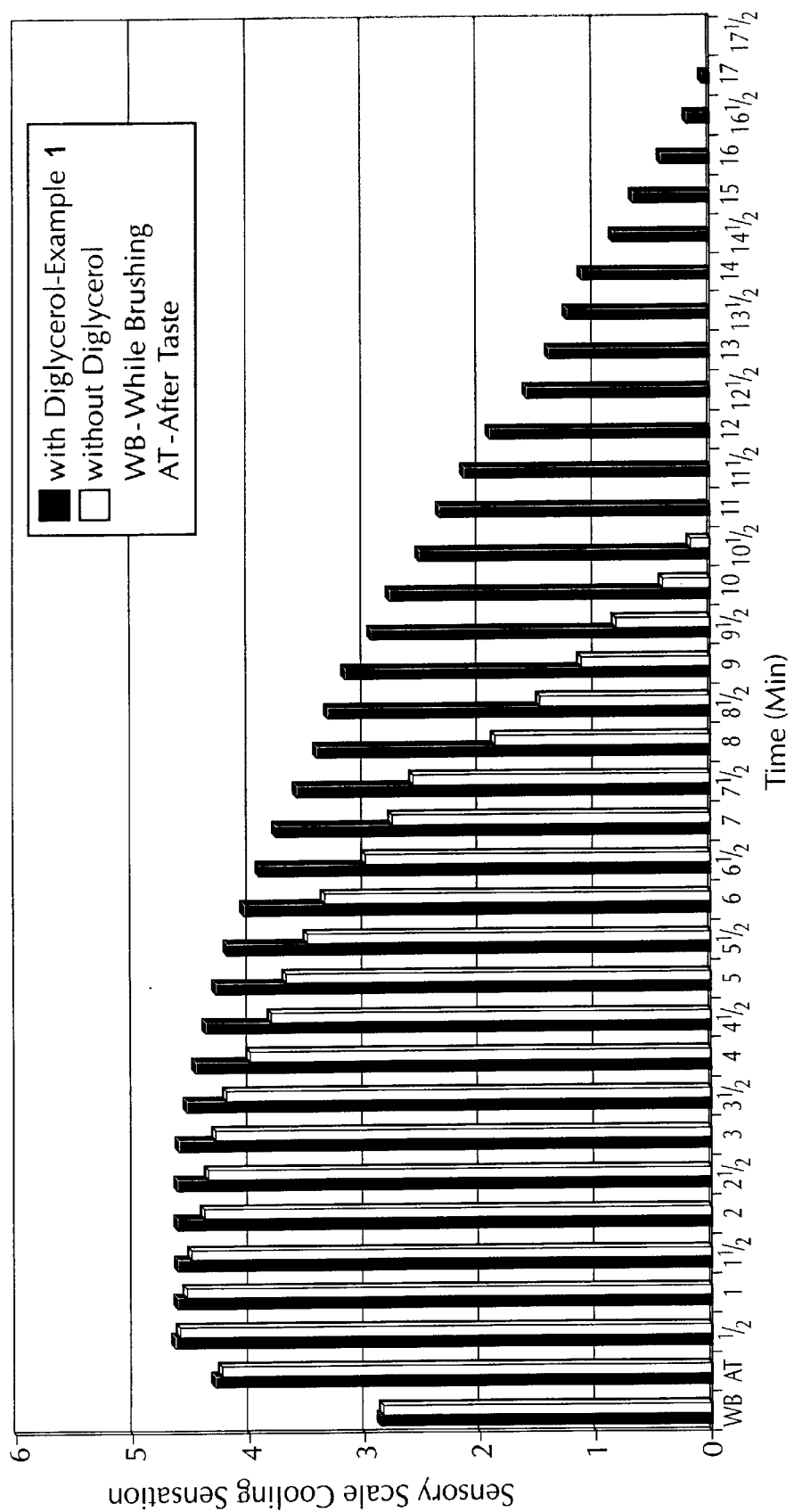
FIG. 1 is a graph depicting cooling perception over time for a flavored mouth rinse of the invention comprising diglycerol and a comparative mouth rinse composition that does not comprise diglycerol.

The oral care compositions comprise about 2.0% to about 75.0% humectants, comprising at least diglycerol. The humectant used in the system may comprise from about 5% to 100% diglycerol (based on the total weight of humectant material in the composition) and up to about 95% other humectants (based on the total weight of humectant material in the composition), and the range for the amount of diglycerol present in the oral care compositions is from about 0.1% to about 75.0%. The other humectants include substances selected from the group consisting of edible polyhydric alcohols, polyols such as glycerol, propylene glycol, propylene glycol glycerol, polyethylene glycol, isomalt, xylitol, maltitol, sorbitol, mannitol and the like, and combinations thereof. Diglycerol is a polyol consisting of two molecules of glycerol bonded by an ether linkage and is available from Solvay Interox, Inc., Houston, Tex. U.S.A. Polyhydric alcohols and polyols are generally available from SPI Polyols, Inc., New Castle, Del., U.S.A., and glycerol is available from many sources including Rierden Chemicals Trading Company, Libertyville, Ill., U.S.A. One embodiment of the invention is where the amount of diglycerol in the oral care composition is between about 5.0% and 45.0%. Another embodiment of the invention is where the total amount of humectants in the oral care composition is between about 25% and about 75%.

The oral care compositions may also comprise from about 5.0% to about 80.0% water, about 0.05% to about 2.00% flavoring agents, and about 0.05% to about 10.0% active compounds. In addition, the oral care compositions may comprise other ingredients selected from the group consisting of emulsifier, alcohol, sweeteners, thickening agents, surfactants, astringent and toning drug extracts, flavor correctants, abrasives or polishes, deodorizing agents, preservatives, flavoring buffers, whitening agents, wound-healing and inflammation inhibiting substances, colorants, dyes, pigments, abrasives, polishes, antimicrobial agents, pH buffers, and the like and combinations thereof, as well as other additives and fillers, the selection and amount of which will depend on the nature of the oral care composition.

Flavoring agents useful for the invention are any food grade or pharmaceutically acceptable flavoring agent, and the specific flavoring agents will depend on the type of oral care composition. Preferably, the flavoring agent comprises natural flavoring oils, including those selected from the group consisting of oil of peppermint, oil of wintergreen, oil of spearmint, clove bud oil, parsley oil, eucalyptus oil and the like. Combinations of oils can also be used. The flavoring agents may comprise compounds selected from the group consisting of menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal and the like, and combinations thereof. The flavoring agent may comprise combinations of natural flavoring oils and other flavoring agents such as the compounds identified above. Also, the flavoring agent may comprise cooling agents such as menthol, N-substituted p-menthane-3-carboxamides (such as N-ethyl p-menthane-3-carboxamide), 3,1-methoxy propane 1,2-diol and the like, or combinations thereof.

The active compounds of the oral care composition will depend on the nature and use of the composition. In general, the active compounds for oral care compositions mask oral malodor, attack the chemicals that bring about the oral malodor, kill or inhibit growth of the bacteria in the mouth that cause breath malodor or halitosis, attack tartar, remove dirt from the teeth and mouth and/or whiten teeth. For example, in embodiments of the invention where the oral care compositions are in the form of mouthwashes, mouth rinses, gums, mouth sprays, lozenges and the like, the active components may include oral hygiene actives, antibacterial substances, desensitizing agents, antiplaque agents and combinations thereof, such as those selected from the group consisting of chlorine dioxide, fluoride, alcohols, triclosan, domiphen bromide, cetyl pyridinium chlorine, calcium lactate, calcium lactate salts and the like, and combinations thereof. In embodiments of the invention where the oral care compositions are in the form of dentrifices, such as toothpaste, gels, and the like, the active components may include oral hygiene actives, antibacterial substances, desensitizing agents, antiplaque agents and combinations thereof, such as those selected from the group consisting of sodium fluoride, stannous fluoride, sodium monofluorophosphate, triclosan, cetyl pyridium chloride, zinc salts, pyrophosphate, calcium lactate, calcium lactate salts, 1-hydroxyethane-1,2-diphosphonic acid, 1-phosphonopropane-1,2,3-tricarboxylic acid, azacycloalkane-2,2-diphosphonic acids, cyclic aminophosphonic acids and the like, and combinations thereof.

Typical mouthwash, mouth rinse, mouth spray, gum and lozenge compositions will comprise about 30% to about 80% water, about 2% to about 35% humectant comprising at least diglycerol, about 1% to about 10% active compounds, about 0.01% to about 0.50% of at least one sweetener, about 0.01% to about 0.50% of at least one thickening agent or binder which may be dispersed in about 2.5% to about 10% of a carrier, such as glycerol, polyethylene glycol (e.g. PEG-400) or combinations thereof, about 0.03% to about 3% of at least one surfactant and about 0.01% to about 1% of at least one flavoring agent. Optionally, the typical mouthwash, mouth rinse, mouth spray, gum or lozenge compositions can comprise about 0.01% to about 1.0% colorants, which includes dyes and pigments and about 0.01% to about 1.0% clouding agents. The compositions may further comprise about 0.01% to about 1.0% titanium dioxide (such as U.S.P. grade available from Whittaker, Clark & Daniels, South Plainfield, N.J., U.S.A.).

Any food grade and/or pharmaceutically acceptable sweetener maybe used in the mouthwash, mouth rinse, mouth spray, gum or lozenge compositions, including saccharin, fructose, xylitol, saccharin salts, thaumatin, aspartame, D-tryptophan, dihydrochalcones, acesulfame and cyclamate salts, especially sodium cyclamate and sodium saccharin, and combinations thereof. Food grade and/or pharmaceutically acceptable coloring agents, or colorants, as would be understood to one skilled in the art, can be used in these compositions, including Food, Drug and Cosmetic (FD&C) colorants such as primary FD&C Blue No. 1, FD&C Blue No. 2, FD&C Green No. 3, FD&C Yellow No. 5, FD&C Yellow No. 6, FD&C Red No. 3, FD&C Red No. 33 and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 33, FD&C Red No. 40 and combinations thereof. Like colorants and dyes may also be used.

Any food grade or pharmaceutically acceptable thickening agent or binder may be used in the mouthwash, mouth rinse, mouth spray, gum or lozenge compositions. The thickening agent or binder may be dispersed in a carrier, such as glycerol, polyethylene glycol or combinations thereof (thickening agent/carrier dispersion). Thickening agents and binders are those selected from the group consisting of xanthan gum, polymeric polyester compounds, natural gums (e.g. gum karaya, gum arabic, gum tragacanth), carrageenan, hydroxymethyl cellulose, methyl cellulose, carboxymethylcellulose, arrowroot powder, starches, particularly corn starch and potato starch and the like, and combinations thereof. The thickening agent or binder may be used with or without a carrier, however, when a carrier is used, up to about 5% thickening agent or binder, preferably from about 0.1% to about 1.0%, is combined with about 95.0% to about 99.9% carrier, preferably about 99.0% to about 99.9%, based on the total weight of the thickening agent/carrier combination.

Clouding agents that may be used in the mouthwash, mouth rinse, mouth spray, gum or lozenge compositions include those selected from the group consisting of calcium citrate, esters of wood rosin, vegetable gum emulsion, caprylic/capric triglycerides, certain gums like guar gum or gum arabic and high-stability oils. Caprylic/capric triglyceride clouding agents are available from Stepan Company, Northfield, Ill., U.S.A. under the trade name NEOBEE®.

In another embodiment of the invention, the oral care composition is in the form of a dentifrice, such as toothpaste or gels. Toothpaste and gels are generally understood to be paste-like or gel-like preparations that are applied directly to the teeth generally by brushing, and dentifrices may be a combination of pastes and gels, as well as combinations of gels or toothpaste with mouthwashes or mouth rinses.

Gums and lozenges may also be used as dentifrices provided that these include the active ingredients normally associated with dentifrice compositions. The gums and lozenges of the invention also comprise the humectant having at least diglycerol.

The dentifrice composition will generally comprise from about 5% to about 20% water, about 5% to about 75% humectant comprising at least diglycerol, about 0.25% to about 3.0% of at least one thickening agent or binder which may be dispersed in about 2.5% to about 10% of a carrier, such as glycerol, polyethylene glycol (e.g. PEG-400), or combinations thereof, about 0.01% to about 0.05% sweeteners, about 5% to about 40% abrasives and polishes, about 0.5% to about 3.0% surfactants, about 0.01% to about 10.0% active compounds which may include oral hygiene actives, antibacterial substances, desensitizing agents, antiplaque agents and combinations thereof, and about 0.25% to about 3.0% flavoring agents. The dentifrice compositions may also comprise fillers and additives, such as about 0.05% to about 1.0% preservative and/or antimicrobial agents, about 0.50% to about 10.0% buffers, about 0.05% to about 5.0% wound healing and inflammation-inhibiting substances, about 0.01% to about 2.0% colorants, such as colors, dyes or particles for special effects, and from about 0.05% to about 10.0% whitening agents, such as hydrogen peroxide and pyrophosphates.

The thickening agent or binder for the dentifrice, may be selected from the group consisting of finely particulate gel silicas and nonionic hydrocolloids, such as carboxmethyl cellulose, sodium hydroxymethyl cellulose, hydroxyethyl cellulose, hydroxypropyl guar, hydroxyethyl starch, polyvinyl pyrrolidone, vegetable gums, such as tragacanth, agar agar, carrageenans, gum arabic, xanthan gum, guar gum, locust bean gum, carboxyvinyl polymers, fumed silica, silica clays and the like and combinations thereof. A preferred thickening agent is carrageenan available under the trade names GELCARIN® and VISCARIN® from FMC Biopolymers, Philadelphia, Pa., U.S.A. Other thickening agents or binders are polyvinyl pyrrolidone available from Noveon, Inc. Cleveland, Ohio, U.S.A. under the trademark CARBOPOL®, fumed silica under the trademark CAB-O-SIL® available from Cabot Corporation, Boston, Mass., U.S.A. and silica clays available from Laporte Industries, Ltd., London, U.K. under the trademark LAPOINTE®. The thickening agent or binder may be used with or without a carrier, such as glycerol, polyethylene glycol (e.g. PEG-400), or combinations thereof, however, when a carrier is used, up to about 5% thickening agent or binder, preferably from about 0.1% to about 1.0%, is combined with about 95.0% to about 99.9% carrier, preferably about 99.0% to about 99.9%, based on the total weight of the thickening agent/carrier combination.

Any food grade and/or pharmaceutically acceptable sweetener maybe used in the toothpaste, gels or tooth powders including saccharin, fructose, xylitol, saccharin salts, thaumatin, aspartame, D-tryptophan, dihydrochalcones, acesulfame and cyclamate salts, especially sodium cyclamate and sodium saccharin, and combinations thereof. The sweetener must be selected such that it does not promote tooth decay.

Any of the customary abrasives or polishes may be used, including those selected from the group consisting of chalk, calcium carbonate, dicalcium phosphate, insoluble sodium metaphosphate, aluminum silicates, calcium pyrophosphate, finely particulate synthetic resins, silicas, aluminum oxide, aluminum oxide trihydrate, hydroxyapatite, and the like, or combinations thereof. The abrasive or polishes may, preferably be, completely or predominantly finely particulate xerogel silica, hydrogel silica, precipitated silica, aluminum oxide trihydrate and finely particulate aluminum oxide or combinations thereof. Silicas available from J. H. Huber Corporation, Havre de Grace, Md., U.S.A. under the trade names ZEOFREE® and ZEODENT® may be used in the invention.

Surfactants useful in the toothpastes or gels, are those selected from the group consisting of anionic high-foam surfactants, such as linear sodium $C_{12-18}$ alkyl sulfates; sodium salts of $C_{12-16}$ linear alkyl polyglycol ether sulfates containing from 2 to 6 glycol ether groups in the molecule; alkyl-($C_{12-16}$)-benzene sulfonates; linear alkane-($C_{12-18}$)-sulfonates; sulfosuccinic acid mono-alkyl-($C_{12-18}$)-esters; sulfated fatty acid monoglycerides; sulfated fatty acid alkanolamides; sulfoacetic acid alkyl-($C_{12-18}$)-esters; and acyl sarcosides, acyl taurides and acyl isothionates all containing from 8 to 18 carbon atoms in the acyl moiety. Nonionic surfactants, such as ethoxylates of fatty acid mono- and diglycerides, fatty acid sorbitan esters and ethylene oxide-propylene oxide block polymers are also suitable. Particularly preferred surfactants are sodium lauryl sulfate and sacrosinate. Combinations of surfactants can be used.

Preservatives and antimicrobial agents that may be used in the toothpaste or gels include those selected from the group consisting of p-hydroxybenzoic acid, methyl, ethyl or propyl ester, sodium sorbate, sodium benzoate, bromochlorophene, phenyl salicylic acid esters, thymol, and the like, and combinations thereof. Suitable pH buffers include those selected from the group consisting of primary, secondary or tertiary alkali phosphates, citric acid, sodium citrate, and the like or combinations thereof. Wound healing and inflammation inhibiting substances include those selected from the group consisting of allantoin, urea, azulene, camomile active substances and acetyl salicylic acid derivatives, and the like, or combinations thereof.

Colorants, that is, colors, dyes, pigments and particulate substances, may be used in the toothpaste or gels. An example of a pigment is titanium dioxide (such as U.S.P. grade available from Whittaker, Clark & Daniels) to provide a bright white color. Food grade and/or pharmaceutically acceptable coloring agents, dyes, or colorants, as would be understood to one skilled in the art, can be used in these compositions, including FD&C colorants including primary FD&C Blue No. 1, FD&C Blue No. 2, FD&C Green No. 3, FD&C Yellow No. 5, FD&C Yellow No. 6, FD&C Red No. 3, FD&C Red No. 33 and FD&C Red No. 40 and lakes FD&C Blue No. 1, FD&C Blue No. 2, FD&C Yellow No. 5, FD&C Yellow No. 6, FD&C Red No. 2, FD&C Red No. 3, FD&C Red No. 33, FD&C Red No. 40 and combinations thereof.

It has been discovered that incorporation of diglycerol in oral care compositions provides an enhanced long lasting smooth effect and longer flavor and cooling sensation, and that the oral care compositions comprising diglycerol maintain enhanced smoothness effect and the longer flavor and cooling sensation on the teeth and gums. While not wishing to be bound to any theory, the enhanced smoothness effect and longer flavor and cooling sensation may be the result of the size of the diglycerol molecule and its interaction with the flavoring and cooling agents after application. Diglycerol is a relatively large molecule compared to humectants traditionally used in oral care compositions, such as glycerol, and thus does not dissolve at as high of a rate as traditional humectants. Because of the size of the diglycerol molecule, it will bind the flavoring agents which may also comprise cooling agents, on the teeth and gums after application and because the dissolution rate is slower, the flavoring agent is maintained on the surface of the teeth and gums thus enhancing the effects. Diglycerol also does not absorb moisture from the gums like other humectants, such as glycerol, which may also enhance the smoothness effects of the oral care compositions.

Diglycerol provides a further advantage when used in oral care compositions in the form of clear gels. Clear gels generally have a refractive index between about 1.44 and about 1.45. The refractive index of diglycerol is 1.49 which allows for clear gel formulations with more water than formulations comprising traditional oral care humectants, such as glycerol that has a refractive index of 1.48.

EXAMPLES

The invention is further described in the following non-limiting examples. In these examples, the oral care compositions may not comprise active components or other ingredients that are not essential to the long lasting smoothness and enhanced flavoring and cooling effects unexpectedly resulting from the incorporation of diglycerol in the compositions.

Example 1

Comparison of Diglycerol vs. No Diglycerols

In this example, a peppermint flavored mouth rinse gel was prepared having the composition set forth in Table 1.

TABLE 1

| INGREDIENT | | WT % |
|---|---|---|
| Polyethylene Glycol | | 3.00 |
| Carboxymethyl Cellulose | | 0.50 |
| Carrageenan | | 0.30 |
| Diglycerol | | 30.00 |
| Saccharin | | 0.30 |
| Licorice Extract | | 0.20 |
| Silica | | 15.00 |
| Pigments | | 1.01 |
| Titanium Dioxide | | 0.10 |
| Sorbitol | | 36.20 |
| Flavoring | | 2.00 |
| Surfactant | | 1.15 |
| Water | QS | 100.00 |

The mouth rinse gel was made by combining various separately prepared phases, as follows.

1. A first phase was prepared by dispersing carboxymethyl cellulose (CMC-12M31XP from Hercules Incorporated) and carrageenan (GELCARIN® DG from FMC Biopolymer) in polyethylene glycol (PLURACOL® E400 from BASF).

2. A second phase was prepared by combining 50 grams of water (10% of the total composition) and the diglycerol (from Solvay Interox, Inc.), then dissolving saccharin and licorice extract (MAGNASWEET® 120 from Mafco Worldwide, Camden, N.J., U.S.A.) and heating to 60° C. The first phase was then added to the second while at 60° C. and the phases were mixed for about 20 to about 30 minutes, and then this mixture was transferred to a model LDM 1 quart double planetary mixer available from Charles Ross & Son Co., Hauppauge, N.Y., U.S.A. (referred to in this Specification as the "Ross Mixer").

3. A third phase was prepared by combining 50 grams (10% of the total composition) of ZEOFREE® 153 and 25 grams (5% of the total composition) of ZEODENT® 113 silica (available from J. M. Huber Corporation), 5 grams (1% of the total composition) of TIMIRON® MP-49 pigment (from EM Industries Inc., Hawthorne, N.Y., U.S.A.), 0.01 grams (0.05% of the total composition) of Mica Black pigment (from EM Industries Inc.) and titanium dioxide (U.S.P. grade from Whittaker, Clark & Daniels). This combination was then added with mixing over a 15 minute period in the Ross Mixer. Once this was added to the Ross Mixer, mixing continued for an additional 15 minutes at a vacuum of 30 inches Hg.

4. A fourth phase was made by dispersing the silica thickener (CAB-O-SIL® M5 available from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.

5. The flavoring (peppermint was used in this example) was then added to the Ross Mixer and mixing continued for an additional 10 minutes at a vacuum of 30 inches Hg.

6. A fifth phase was prepared by dissolving the surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was released and the resulting mouth rinse gel was transferred to storage containers.

The mouthrinse gel was tested by an expert panel trained in sensory perception. Each panelist applied the mouthrinse gel by placing a quantity of gel into the mouth, moving the gel past the teeth and gums and expectorating. The panelists were then asked to record the cooling sensation every 30 seconds for a total of 17½ minutes based on the following scale:

0–2: very low perception of cooling

2–4: medium perception of cooling

4–6: high perception of cooling.

A comparative formulation not containing diglycerol was also evaluated on the same scale. The results are set forth in FIG. 1. As can be seen from the data of FIG. 1, the mouthrinse gel containing diglycerol exhibited higher perception of cooling throughout the duration of the test as compared with the mouthrinse gel which does not contain diglycerols. In addition, the length of time for cooling perception was unexpectedly 56.5% longer for the diglycerol containing toothpaste gel compared to the toothpaste gel without diglycerol (i.e. 17 minutes vs. 10½ minutes).

Examples 2A and 2B

Comparison of Diglycerol vs. Glycerol

In this example, a gel toothpaste formulation was made except that diglycerol (Example 2A) was substituted for glycerol (Example 2B) as a humectant in the composition. The gel toothpaste formulation prepared for this example had the composition set forth in Table 2.

TABLE 2

| Ingredients | Example 2A (% wt.) | Example 2B (% wt.) |
|---|---|---|
| Polyethylene glycol 400 (PEG-400) | 3.00 | 3.00 |
| Sodium Carboxymethylcellulose | 1.20 | 1.20 |
| Carrageenan | 0.30 | 0.30 |
| Diglycerol | 35.99 | — |
| Glycerol | — | 35.99 |
| Sodium saccharin | 0.30 | 0.30 |
| Magnasweet 120 | 0.50 | 0.50 |
| Hydrated silica | 15.00 | 15.00 |
| Sorbitol 70% | 25.00 | 25.00 |
| Fumed Silica | 0.25 | 0.25 |
| Flavoring | 1.20 | 1.20 |
| Sodium Lauryl Sulfate | 1.15 | 1.15 |
| Titanium Dioxide | 0.10 | 0.10 |
| Deionized Water | 16.01 | 16.01 |
| Total | 100.00 | 100.00 |

The gel toothpaste formulation was tested by an expert panel trained in sensory perception. Each panelist applied the gel toothpaste by placing a quantity of gel into the mouth via a toothbrush, moving the gel past the teeth and gums and expectorating. The panelists were then asked to record the cooling sensation every 30 seconds for a total of 17½ minutes based on the following scale:

0–2: very low perception of cooling

2–4: medium perception of cooling

4–6: high perception of cooling.

Figure 2:
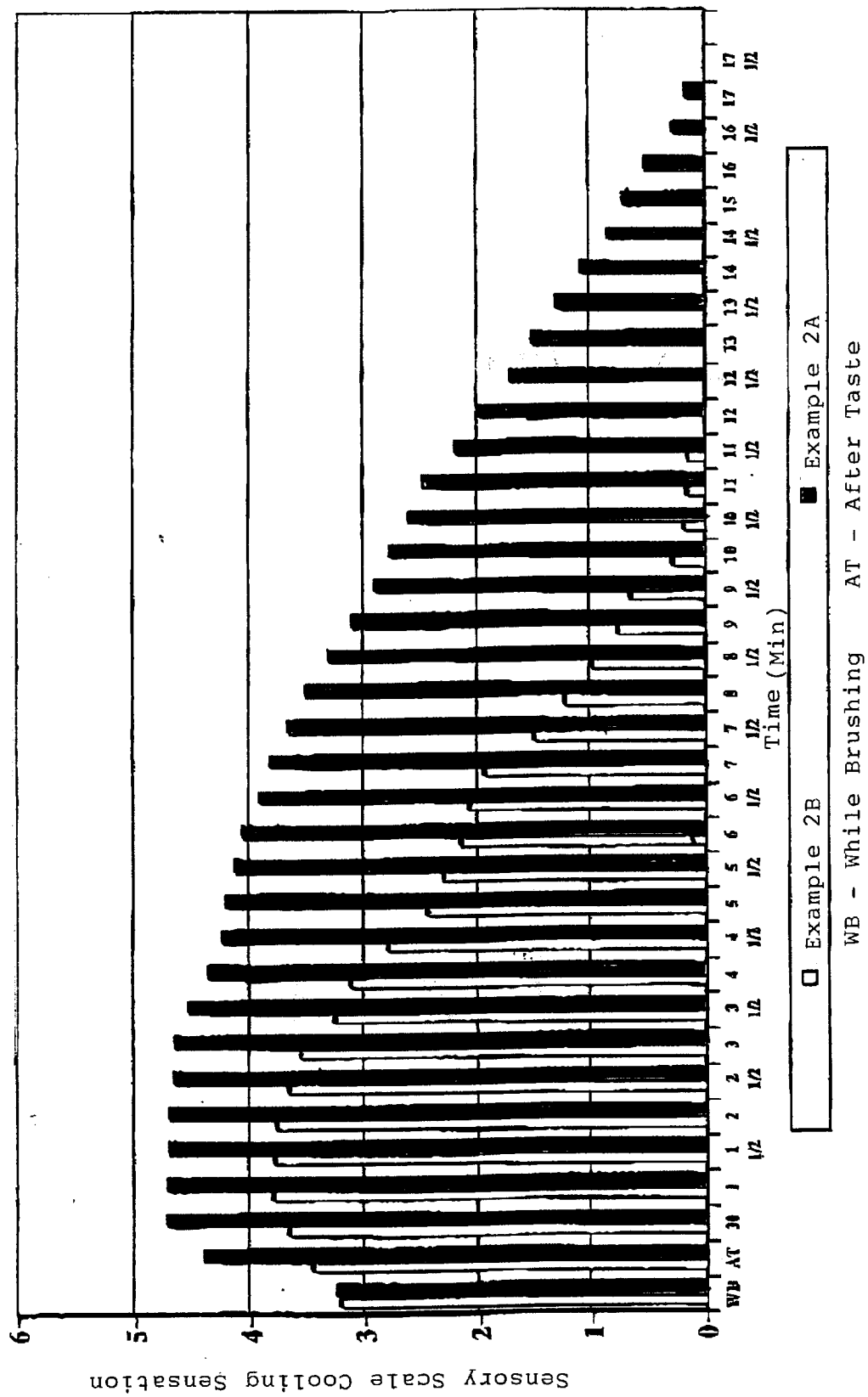
FIG. 2 is a graph depicting cooling perception over time for a flavored toothpaste of the invention comprising diglycerol and a comparative toothpaste composition that does not comprise diglycerol.

The results are set forth in FIG. 2. As can be seen from FIG. 2, the diglycerol containing toothpaste gel unexpectedly exhibited higher perception of cooling throughout the duration of the test as compared with the glycerol containing toothpaste gel. In addition, the length of time for cooling perception was unexpectedly 47.8% longer for the diglycerol containing toothpaste gel compared to the glycerol containing toothpaste gel (i.e. 17 minutes vs. 11½ minutes).

Example 2C

Comparison of Diglycerol vs. Glycerol

A dentifrice gel formulation was made except that diglycerol was substituted for glycerol as a humectant in the composition. The dentifrice gel formulation prepared for this example had the composition set forth in Table 2C.

TABLE 2C

| INGREDIENT | | WT % |
|---|---|---|
| Polyethylene Glycol | | 3.00 |
| Carboxymethyl Cellulose | | 1.20 |
| Carrageenan | | 0.30 |
| Diglycerol | | 37.60 |
| Sodium Benzoate | | 0.20 |
| Sweetener | | 0.20 |
| Colorant | | 0.10 |
| Silica | | 10.00 |
| Sorbitol | | 30.00 |
| Silica Thickener | | 0.25 |
| Flavoring | | 1.00 |
| Surfactant | | 1.15 |
| Water | QS | 100. |

The dentifrice gel was made by combining various separately prepared phases, as follows.

1. A first phase was prepared by dispersing carboxymethyl cellulose (CMC-12M31XP available from Hercules Incorporated, Wilmington, Del., U.S.A.) and carrageenan (GELCARIN® DG from FMC Biopolymer) in polyethylene glycol (PLURACOL® E400, from BASF, Mt. Olive, N.J., U.S.A.)

2. A second phase was prepared by combining 50 grams of water (10% of the total composition) and diglycerol (from Solvay Interox, Inc.), then dissolving saccharin and sodium benzoate (from Mallinckrodt Baker, Inc., Phillipsburg, N.J., U.S.A.), then adding colorant (FD&C Blue No.1 dye) and heating to 60° C. The first phase was then added to the second while at 60° C. and the phases were mixed for about 20 to about 30 minutes, and then this mixture was transferred to the Ross Mixer.

3. A third phase was prepared by combining 25 grams (5% of the total composition) of ZEOFREE® 153 and 25 grams (5% of the total composition) of ZEODENT® 113 silica (from J.M. Huber Corporation). The silica was then added with mixing over a 15 minute period to the Ross Mixer. Once the silica was added to the Ross Mixer, mixing continued for an additional 15 minutes at a vacuum of 30 inches Hg.

4. A fourth phase was made by dispersing silica thickener (CAB-O-SIL® M5 from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.

5. The flavoring was then added to the Ross Mixer and mixing continued for an additional 10 minutes at a vacuum of 30 inches Hg.

6. A fifth phase was prepared by dissolving surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was released and the resulting dentifrice gel was transferred to storage containers.

The dentifrice gel was tested for flavoring and cooling effects by a panel of experts trained in sensory perception. Each panelist applied the dentifrice gel to the teeth and gums with a toothbrush and rinsed. A prolonged smoothness and enhanced flavoring effect on the teeth and gums was experienced.

Examples 3A and 3B
(Comparison of Diglycerol vs. Glycerol)

Peppermint flavored mouthwash formulations were prepared having the formulas set forth in Table 3. The mouthwash formulation of example 3A is prepared in accordance with the invention having humectant diglycerol. Example 3B is a comparative example having mouthwash prepared with glycerol as the humectant.

TABLE 3

| INGREDIENTS | WT % | |
|---|---|---|
| | Example 3A | Example 3B (Comparative) |
| Glycerol (Carrier) | 10.00 | 10.00 |
| Xanthan Gum | 0.12 | 0.12 |
| Water | 69.08 | 69.08 |
| Diglycerol | 20.00 | — |
| Glycerol | — | 20.00 |
| Saccharin | 0.10 | 0.10 |
| Titanium Dioxide | 0.10 | 0.10 |
| Surfactant | 0.45 | 0.45 |
| Flavoring | 0.15 | 0.15 |
| Total | 100.25 | 100.25 |

The mouthwash formulations were prepared by making first phases by combining water and humectant and then dissolving the saccharin. The humectant used for example 3A, which was made in accordance with the invention, was diglycerol (from Solvay Interox, Inc.) and glycerol was used as the humectant for the comparative example (Example 3B). Next, second phases were prepared by dispersing the thickening agent (xanthan gum) in carrier (glycerol), and then the second phases were added to each first phase. Titanium dioxide (U.S.P. grade from Whittaker, Clark & Daniels) was then added to each of the combined first and second phases and mixed for 5 minutes at ambient temperature. Flavoring (peppermint was used for this example) was added to surfactant (CREMOPHOR® RH-40 from BASF) to obtain third phases. The combined titanium dioxide and first and second phases were added to the third phases to obtain the compositions of example 3A and example 3B.

The mouthwash formulation was tested by an expert panel trained in sensory perception. These samples were separately applied to the teeth and gums of each expert panelist by placing a quantity in the mouth, moving the mouth rinse past the teeth and gums a plurality of times and expectorating. Water was used to rinse the mouth between application of examples 3A and 3B. The panelists were then asked to record the cooling sensation every 30 seconds for a total of 17½ minutes based on the following scale:

0–2: very low perception of cooling
2–4: medium perception of cooling
4–6: high perception of cooling.

Figure 3:
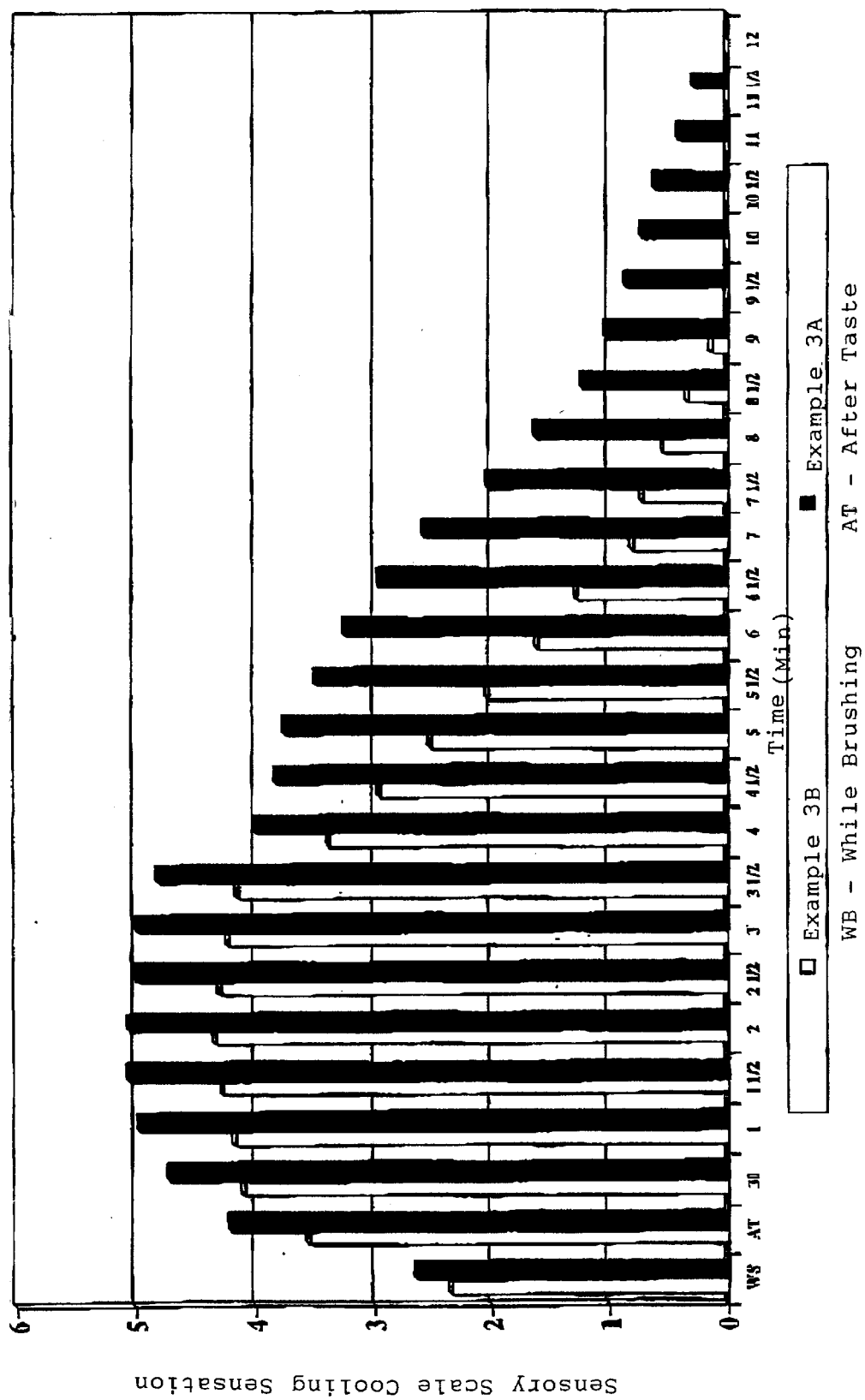
FIG. 3 is a graph depicting cooling perception over time for a flavored mouthwash of the invention comprising diglycerol and a comparative mouthwash composition that does not comprise diglycerol.

The results are set forth in FIG. 3. As can be seen from FIG. 3, the mouthwash formulation having diglycerol humectant unexpectedly exhibited higher perception of cooling throughout the duration of the test as compared with the mouthwash formulation having glycerol humectant. In addition, the length of time for cooling perception was unexpectedly 27.8% longer for the diglycerol containing mouthwash compared to the glycerol containing mouthwash (i.e. 11½ minutes vs. 9 minutes).

Examples 4A and 4B
(Comparison of Diglycerol vs. Sorbitol)

Mouth rinse formulations were prepared having the formulas set forth in Table 4. The mouth rinse formulation of example 4A is prepared in accordance with the invention having humectant diglycerol. Example 4B is a comparative example having mouth rinse prepared with sorbitol as the humectant.

TABLE 4

| INGREDIENTS | WT % | |
|---|---|---|
| | Example 4A | Example 4B (Comparative) |
| Glycerol (Carrier) | 10.00 | 10.00 |
| Xanthan Gum | 0.12 | 0.12 |
| Water | 69.08 | 69.08 |
| Diglycerol | 20.00 | — |
| Sorbitol | — | 20.00 |
| Saccharin | 0.10 | 0.10 |
| Titanium Dioxide | 0.10 | 0.10 |
| Surfactant | 0.45 | 0.45 |
| Flavoring | 0.15 | 0.15 |
| Total | 100.25 | 100.25 |

The mouth rinse formulations were prepared by making first phases by combining water and humectant and then dissolving the saccharin. The humectant used for example 4A, which was made in accordance with the invention, was diglycerol (from Solvay Interox, Inc.) and sorbitol was used as the humectant for the comparative example (Example 4B). Next, second phases were prepared by dispersing the thickening agent (xanthan gum) in carrier (glycerol), and then the second phases were added to each first phase. Titanium dioxide (U.S.P. grade from Whittaker, Clark & Daniels) was then added to each of the combined first and second phases and mixed for 5 minutes at ambient temperature. Flavoring was added to surfactant (CREMOPHOR® RH-40 from BASF) to obtain third phases. The combined titanium dioxide and first and second phases were added to the third phases to obtain the compositions of example 4A and example 4B.

Examples 4A and 4B were evaluated by an expert panel of 10 individuals. These samples were separately applied to the teeth and gums of each expert panelist by placing a quantity in the mouth, moving the mouth rinse past the teeth and gums a plurality of times and expectorating. Water was used to rinse the mouth between application of examples 4A and 4B. Each panelist was asked to report the total time that a cooling effect was experienced in the mouth for each sample. The average time for cooling effect experienced by the panelists was about 30 minutes for Sample 4A and about 10 minutes for sample 4B.

Examples 5A, 5B and 5C (Comparison of Diglycerol or Diglycerol/Sorbitol vs. Sorbitol)

Mouth rinse formulations were prepared having the formulas set forth in Table 5. The mouth rinse formulation of Example 5A is prepared in accordance with the invention having diglycerol as the humectant, and Example 5B is prepared in accordance with the invention with the humectant comprising both diglycerol and sorbitol. Example 5C is a comparative example having sorbitol humectant and no diglycerol in the composition.

TABLE 5

|  | WT % | | |
|---|---|---|---|
| INGREDIENTS | Example 5A | Example 5B | Example 5C (Comparative) |
| Glycerol (Carrier) | 10.00 | 10.00 | 10.00 |
| Xanthan Gum | 0.12 | 0.12 | 0.12 |
| Water | 69.08 | 69.08 | 69.08 |
| Diglycerol | 20.00 | 10.00 | — |
| Sorbitol | — | 10.00 | 20.00 |
| Saccharin | 0.10 | 0.10 | 0.10 |
| Titanium Dioxide | 0.10 | 0.10 | 0.10 |
| Surfactant | 0.45 | 0.45 | 0.45 |
| Flavoring | 0.15 | 0.15 | 0.15 |
| Total | 100.00 | 100.00 | 100.00 |

The mouth rinse formulations were prepared by making first phases by combining water and the respective humectant for each sample then dissolving the saccharin. Diglycerol (from Solvay Interox, Inc.) was used for example 5A, a combination of diglycerol (from Solvay Interox, Inc.) and sorbitol was used for example 5B and sorbitol was used for example 5C. Next, second phases were prepared by dispersing the thickening agent (xanthan gum) in carrier (glycerol), and then the second phases were added to each first phase. Then, titanium dioxide (U.S.P. grade from Whittaker, Clark & Daniels) was added to the combined first and second phases and mixed for 5 minutes at ambient temperature. Next, flavoring was added to the surfactant (CREMOPHOR® RH-40 from BASF) to obtain third phases. The combined titanium dioxide, first phases and second phases were added to the third phases to obtain the compositions of example 5A, 5B and 5C.

Examples 5A, 5B and 5C were evaluated by an expert panel of 10 panelists. The panelists applied each sample to the teeth and gums by placing a quantity in the mouth, moving the mouth rinse past the teeth and gums a plurality of times and expectorating. Water was used to rinse the mouth between the application of each sample. Each panelist was asked to report the total time that a cooling effect was experienced in the mouth for each sample. The average time for cooling effect experienced by the panelists was about 30 minutes for example 5A, about 20 minutes for example 5B and about 5 minutes for example 5C.

Example 6

In this example, an opacified gel was prepared having the composition set forth in Table 6.

TABLE 6

| INGREDIENT | WT % |
|---|---|
| Polyethylene Glycol | 3.00 |
| Carboxymethyl Cellulose | 1.20 |
| Carrageenan | 0.30 |
| Diglycerol | 37.60 |
| Silica Thickener | 0.25 |
| Sodium Benzoate | 0.20 |
| Saccharin | 0.20 |
| Sodium Fluoride | 0.20 |
| Silica | 10.00 |
| Sorbitol | 29.35 |
| Titanium Dioxide | 0.25 |
| Flavoring | 1.00 |
| Surfactant | 1.15 |
| Water | QS 100. |

The opacified gel was made by combining various separately prepared phases, as follows.

1. A first phase was prepared by dispersing carboxymethyl cellulose (CMC-12M31XP from Hercules Incorporated) and carrageenan (GELCARIN® DG from FMC Biopolymer) in the polyethylene glycol (PLURACOL® E400 from BASF).
2. A second phase was prepared by combining 50 grams of water (10% of the total composition) and diglycerol (from Solvay Interox, Inc.), then dissolving saccharin and sodium benzoate (from Mallinckrodt Baker), then adding sodium fluoride and heating to 60° C. The first phase was then added to the second phase while at 60° C. and the phases were mixed for about 20 to about 30 minutes, and then this mixture was transferred to the Ross Mixer.
3. A third phase was prepared by combining 25 grams (5% of the total composition) of ZEOFREE® 153 and 25 grams (5% of the total composition) of ZEODENT® 113 silica (from J.M. Huber Corporation). The silica was then added with mixing over a 15 minute period to the Ross Mixer. Once the silica was added to the Ross Mixer, mixing continued for an additional 15 minutes at a vacuum of 30 inches Hg.
4. A fourth phase was made by dispersing silica thickener (CAB-O-SIL® M5 from Cabot Corporation) in sorbitol, and adding this dispersion to the Ross Mixer, at a pressure of 15 inches Hg, over a period of 15 minutes with mixing. Once the silica thickener and sorbitol dispersion were completely added to the Ross Mixer, mixing of the contents was continued for an additional 15 minutes at a vacuum of 30 inches Hg.
5. The flavoring was then added to the Ross Mixer and mixing continued for an additional 10 minutes at a vacuum of 30 inches Hg.
6. A fifth phase was prepared by dissolving surfactant (sodium lauryl sulfate, STEPANOL® WA100, from the Stepan Company) in 25 grams of water (5% of the total composition). The Ross Mixer was stopped and pressure released and the fifth phase was added to the Ross Mixer. The pressure in the Ross Mixer was then raised to 30 inches Hg and the contents were mixed for 15 minutes after which the pressure was released and the resulting opacified gel was transferred to storage containers.

The gel was tested by an expert panel by applying to the teeth and gums using a toothbrush as described in Example 1. A prolonged smoothness and enhanced cooling and flavoring effect on the teeth and gums were experienced by the panel.

Example 7

In this example, a flavored mouth rinse was prepared having the composition set forth in Table 7.

TABLE 7

| INGREDIENTS | WT % |
|---|---|
| Glycerol (Carrier) | 5.00 |
| Xanthan Gum | 0.12 |
| Water | 63.52 |
| Diglycerol | 15.60 |
| Saccharin | 0.10 |
| Colorant | 0.06 |
| Flavoring | 0.15 |
| Surfactant | 0.45 |
| Alcohol | 15.00 |
| Total | 100.58 |

The mouth rinse was prepared by making a first phase by combining water and diglycerol (from Solvay Interox, Inc.) and dissolving saccharin and colorant (FD&C Blue No. 1 dye). Next, a second phase was made by dispersing the thickening agent (xanthan gum) in carrier (glycerol) and then the second phase was added to the first phase. Next a third phase was prepared by combining the flavoring agent, surfactant (ethoxylated hydrogenated castor oil, CREMOPHOR® RH-40 available from BASF, Mount Olive, N.J., U.S.A.), and alcohol. The combined first and second phases were added to the third phase and then all of the phases were mixed together at ambient temperature for 5 minutes to obtain the mouth rinse.

The mouth rinse was analyzed by an expert panel and applied to the teeth and gums by placing a quantity in the mouth, moving the mouth rinse past the teeth and gums a plurality of times and expectorating. The mouth rinse provided long lasting smoothness, and enhanced cooling and flavoring effects on the teeth and gums.

Example 8

A milky mouthwash, that is a mouth wash having an opaque and cloudy appearance, was made according to the invention by first making a water phase by combining 42.24 grams of diglycerol (from Solvay Interox, Inc.) and 0.30 grams of saccharin with 225.00 grams of water in a mixer and mixing for about 10 minutes at ambient temperature, then adding a thickening agent comprising 0.36 grams of xanthan gum dispersed in 15 grams of carrier (glycerol) with continued mixing for about 5 minutes at ambient temperature then adding 0.30 grams of titanium dioxide (U.S.P. grade from Whittaker, Clark & Daniels) with continued mixing for about 10 minutes at ambient temperature. Separately, an oil phase was made by combining 15 grams of glycerol, 1.35 grams of surfactant (CREMOPHOR® RH-40 from BASF) and 0.45 grams of flavoring in a mixer with mixing for about 10 minutes at ambient temperature. The water phase was then combined with the oil phase in the mixer and mixing continued for about 10 minutes at ambient temperature to obtain the mouthwash composition comprising diglycerol having a cloudy and milky appearance. A long lasting cooling effect was experienced on the teeth and gums.

TABLE 8

| Ingredients | Weight % |
|---|---|
| Diglycerol | 14.08 |
| Saccharin | 0.10 |
| Water | 75.00 |
| Xanthan gum | 0.12 |
| Glycerol (Carrier) | 10.00 |
| Titanium dioxide | 0.10 |
| Cremophor ® RH-40 | 0.45 |
| Flavorant | 0.15 |
| Total | 100.00 |

Example 9

A tinted milky mouthwash was made according to the invention by first making a water phase by combining 42.24 grams of diglycerol, 0.30 grams of saccharin and 0.06 grams of colorant (FD&C Red No. 33 dye) with 225.54 grams of water in a mixer and mixing for about 10 minutes at ambient temperature, then adding a thickening agent comprising 0.36 grams of xanthan gum dispersed in 15 grams of carrier (glycerol) with continued mixing for about 5 minutes at ambient temperature then adding 0.30 grams of titanium dioxide (U.S.P. grade from Whittaker, Clark & Daniels) with continued mixing for about 10 minutes at ambient temperature. Separately, an oil phase was made by combining 15 grams of glycerol, 0.90 grams of surfactant (CREMOPHOR® RH-40 from BASF) and 0.30 grams of flavoring in a mixer with mixing for about 10 minutes at ambient temperature. The water phase was then combined with the oil phase in the mixer and mixing continued for about 10 minutes at ambient temperature to obtain the mouthwash composition comprising diglycerol having a red-tinted cloudy and milky appearance. A long lasting cooling effect was experienced on the teeth and gums.

TABLE 9

| Ingredient | Weight % |
|---|---|
| Diglycerol | 14.08 |
| Saccharin | 0.10 |
| FD & C Red No. 33 dye | 0.02 |
| Water | 75.18 |
| Xanthan gum | 0.12 |
| Glycerol (Carrier) | 10.00 |
| Titanium dioxide | 0.10 |
| Cremophor ® RH-40 | 0.30 |
| Flavorant | 0.10 |
| Total | 100.00 |

I claim:

1. An oral care composition for application to teeth and the gums of a user comprising:
   (a) about 5% to about 80% by weight of water;
   (b) about 2% to about 75% by weight of humectant comprising diglycerol in an amount of about 5% to 100% by weight of the total weight of humectant in the composition;
   (c) about 0.05% to about 20% by weight of flavoring agents; and
   (d) about 0.05% to about 10% by weight of active compounds,
   wherein the diglycerol binds the flavoring agents after application to the teeth and the gums of the user.

2. The composition of claim 1 further comprising other ingredients selected from the group consisting of emulsifiers, alcohols, sweeteners, thickening agents, surfactants, suspending agents, astringent and toning drug extracts, flavor correctants, abrasives or polishes, deodorizing agents, preservatives, flavoring buffers, whitening agents, wound-healing and inflammation inhibiting substances, colorants, dyes, pigments, abrasives, polishes, antimicrobial agents, pH buffers and combinations thereof.

3. The composition of claim 1 wherein the humectant further comprises at least one polyol.

4. The composition of claim 3 wherein the at least one polyol is selected from the group consisting of glycerol, propylene glycol, propylene glycol glycerol, polyethylene glycol, isomalt, xylitol, maltitol, sorbitol, mannitol and combinations thereof.

5. The composition of claim 1 wherein the flavoring agents comprise compounds selected from the group consisting of oil of peppermint, oil of wintergreen, oil of spearmint, clove bud oil, parsley oil, eucalyptus oil, menthol, menthane, anethole, methyl salicylate, eucalyptol, cassia, 1-methyl acetate, sage, eugenol, oxanone, alpha-irisone, marjoram, lemon, orange, propenyl guaethol acetyl, cinnamon, vanilla, thymol, linalool, cinnamaldehyde glycerol acetal, N-substituted p-menthane-3-carboxamides, 3,1-methoxy propane 1,2-dial and combinations thereof.

6. The composition of claim 1 wherein the active compounds are selected from the group consisting of chlorine dioxide, fluoride, alcohols, triclosan, domiphen bromide, cetyl pyridinium chlorine, calcium lactate, calcium lactate salts, sodium fluoride, stannous fluoride, sodium monofluorophosphate, cetyl pyridium chloride, zinc salts, pyrophosphate, 1hydroxyethane-1, 2-diphosphonic acid, 1-phosphonopropane-1,2,3-tricarboxylic acid, azacycloalkane-2,2-diphosphonic acids, cyclic aminophosphonic acids and combinations thereof.

7. The composition of claim 1 in the form of a toothpaste, gel, mouthwash, mouth rinse, gum, mouth spray, lozenge or combinations thereof.

8. Mouthwash, mouth rinse, mouth spray, gum or lozenge compositions for application to teeth and gums of a user comprising:
(a) about 30% to about 80% by weight of water;
(b) about 2% to about 35% by weight of humectant comprising diglycerol;
(c) about 1% to about 10% by weight of active compounds;
(d) about 0.01% to about 0.50% by weight of at least one sweetener;
(e) about 0.01 to about 0.50% by weight of at least one thickening agent;
(f) about 0.1% to about 3% by weight of at least one surfactant; and
(g) about 0.01% to about 1% by weight of at least one flavoring agent,
wherein the diglycerol binds the flavoring agents after application to the teeth and the gums of the user.

9. The compositions of claim 8 further comprising about 0.01% to about 1.0% by weight of colorants, about 0.01% to about 1.0% by weight of clouding agents or about 0.01% to about 1.0% by weight of titanium dioxide.

10. The compositions of claim 8 wherein the thickening agent is selected from the group consisting of xanthan gum, polymeric polyester compounds, natural gums, carrageenan, hydroxymethyl cellulose, methyl cellulose, carboxymethylcellulose, arrowroot powder, starches and combinations thereof.

11. The compositions of claim 10 wherein the thickening agent is dispersed in about 2.5% to about 10% by weight of a carrier.

12. The compositions of claim 11 wherein the carrier is glycerol, polyethylene glycol or combinations thereof.

13. The compositions of claim 8 wherein the active compounds are selected from the group consisting of chlorine dioxide, fluoride, alcohols, triclosan, domiphen bromide, cetyl pyridinium chlorine, calcium lactate, calcium lactate salts and combinations thereof.

14. The compositions of claim 8 wherein the sweeteners are selected from the group consisting of saccharin, fructose, xylitol, saccharin salts, thaumatin, aspartame, D-tryptophan, dihydrochalcones, acesulfame, cyclamate salts, and combinations thereof.

15. The compositions of claim 14 wherein the cyclamate salts are sodium cyclamate or sodium saccharin.

16. The compositions of claim 9 wherein the clouding agents are selected from the group consisting of calcium citrate, esters of wood rosin, vegetable gum emulsions, caprylic/capric triglycerides, guar gum, gum arabic and oils.

17. Dentifrice compositions for application to teeth and gums of a user comprising:
(a) about 5% to about 20% by weight of water;
(b) about 5% to about 75% by weight of humectant comprising diglycerol;
(c) about 0.25% to about 3.0% by weight of at least one thickening agent;
(d) about 0.01% to about 0.50% by weight of sweeteners;
(e) about 5% to about 40% by weight of abrasives or polishes;
(f) about 0.5% to about 3.0% by weight of surfactants;
(g) about 0.01% to about 10% by weight of active compounds; and
(h) about 0.25% to about 3.0% by weight of flavoring agents,
wherein the diglycerol binds the flavoring agent after application to the teeth and the gums of the user.

18. The dentifrice compositions of claim 17 further comprising about 0.05% to about 1.0% by weight of preservatives and/or antimicrobial agents, about 0.5% to about 10% by weight of buffers, about 0.05% to about 5.0% by weight of wound healing and inflammation-inhibiting substances, about 0.01% to about 2.0% by weight of colorants or about 0.5% to about 3.0% by weight of whitening agents.

19. The dentifrice compositions of claim 17 wherein the thickening agent is selected from the group consisting of carboxmethyl cellulose, sodium hydroxymethyl cellulose, hydroxyethyl cellulose, hydroxypropyl guar, hydroxyethyl starch, polyvinyl pyrrolidone, tragacanth, agar, carrageenan, gum arabic, xanthan gum, guar gum, locust bean gum, carboxyvinyl polymers, fumed silica, silica clays and combinations thereof.

20. The dentifrice compositions of claim 19 wherein the thickening agent is dispersed in about 2.5% to about 10% of a carrier.

21. The dentifrice compositions of claim 20 wherein the carrier is glycerol, polyethylene glycol or combinations thereof.

22. The dentifrice compositions of claim 18 wherein the sweeteners are selected from the group consisting of saccharin, fructose, xylitol, saccharin salts, thaumatin, aspartame, D-tryptophan, dihydrochalcones, acesulfame, cyclamate salts and combinations thereof.

23. The dentifrice compositions of claim 22 the cyclamate salts are sodium cyclamate or sodium saccharin.

24. The dentifrice compositions of claim 17 wherein the surfactants are selected from the group consisting of sodium lauryl sulfate, sacrosinate, linear sodium $C_{12-18}$ alkyl sulfates, sodium salts of $C_{12-16}$ linear alkyl polyglycol ether sulfates containing from 2 to 6 glycol ether groups in the molecule, alkyl-($C_{12-16}$)-benzene sulfonates, linear alkane-($C_{12-18}$)-sulfonates, sulfosuccinic acid mono-alkyl-($C_{12-18}$)-esters, sulfated fatty acid monoglycerides, sulfated fatty acid alkanolamides, sulfoacetic acid alkyl-($C_{12-18}$)-esters and acyl sarcosides, acyl taurides and acyl isothionates containing from 8 to 18 carbon atoms in the acyl moiety, ethoxylates of fatty acid mono- and diglycerides, fatty acid sorbitan esters, ethylene oxide-propylene oxide block polymers and combinations thereof.

25. The dentifrice compositions of claim 17 wherein the abrasives or polishes are selected from the group consisting of chalk, calcium carbonate, dicalcium phosphate, aluminum silicates, calcium pyrophosphate, finely particulate synthetic resins, silicas, aluminum oxide, aluminum oxide trihydrate, hydroxyapatite and combinations thereof.

26. The dentifrice compositions of claim 17 wherein the abrasives or polishes are selected from the group consisting of sodium metaphosphate particulates, xerogel silica, hydrogel silica, precipitated silica, aluminum oxide trihydrate, particulate aluminum oxide and combinations thereof.

27. The dentifrice compositions of claim 18 wherein the preservatives and/or antimicrobial agents are selected from the group consisting of p-hydroxybenzoic acid or its methyl ester, ethyl ester or propyl ester, sodium sorbate, sodium benzoate, bromochlorophene, phenyl salicylic acid esters, thymol, and combinations thereof.

28. The dentifrice compositions of claim 18 wherein the buffers are selected from the group consisting of primary, secondary or tertiary alkali phosphates, citric acid, sodium citrate and combinations thereof.

29. The dentifrice compositions of claim 18 wherein the wound healing and inflammation inhibiting substances are selected from the group consisting of allantoin, urea, azulene, camomile active substances, acetyl salicylic acid derivatives and combinations thereof.

30. The dentifrice compositions of claim 18 in the form of toothpastes, gels, gums, lozenges or combinations thereof.

* * * * *

UNITED STATES PATENT AND TRADEMARK OFFICE
CERTIFICATE OF CORRECTION

PATENT NO. : 6,723,304 B2
DATED : April 20, 2004
INVENTOR(S) : Stier

It is certified that error appears in the above-identified patent and that said Letters Patent is hereby corrected as shown below:

Column 17,
Line 25, "1,2-dial" should read -- 1,2-diol --.
Line 32, "1hydroxyethane-1" should read -- "1-hydroxyethane-1" --.

Signed and Sealed this

Twenty-eighth Day of September, 2004

JON W. DUDAS
*Director of the United States Patent and Trademark Office*